Figure 4:
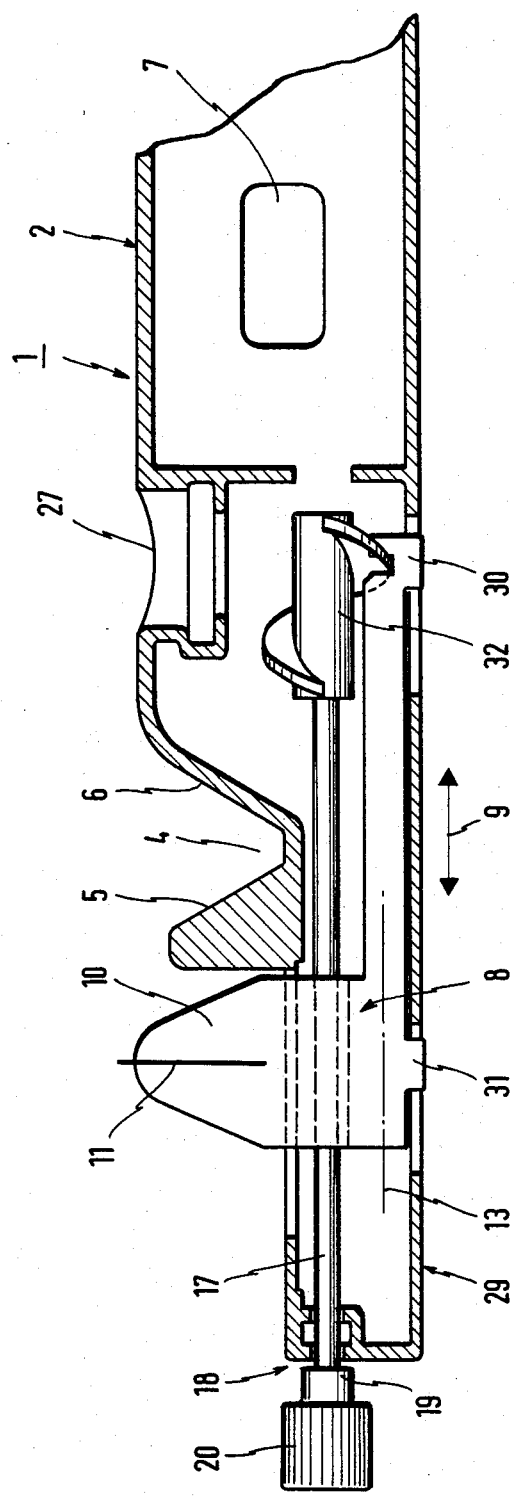

United States Patent [19]

Pehart

[11] Patent Number: 4,514,906
[45] Date of Patent: May 7, 1985

[54] PUPILLARY DISTANCE MEASURING INSTRUMENT

[76] Inventor: Paul Pehart, Kapuzinerstrasse 35, D-8000, Munchen 5, Fed. Rep. of Germany

[21] Appl. No.: 538,081

[22] Filed: Oct. 3, 1983

[51] Int. Cl.³ .............................................. A61B 3/10
[52] U.S. Cl. ........................................ 33/200; 33/512
[58] Field of Search ............................ 33/200, 174 D

[56] References Cited

U.S. PATENT DOCUMENTS 557,220  3/1896  Palmer ................................. 33/200
716,516  12/1902  Boothroyd et al. ................. 33/200

Primary Examiner—Harry N. Haroian

[57] ABSTRACT

An instrument for measuring the distance of the eye from the root of the nose, of the type comprising a sight window for reading the indication of the measured value, a part for resting on the nose and at least one slider provided with a measuring mark, consists of a handle part provided with the sight window and spaced from the part for resting on the nose, and of an adjusting part containing the single slider.

6 Claims, 15 Drawing Figures

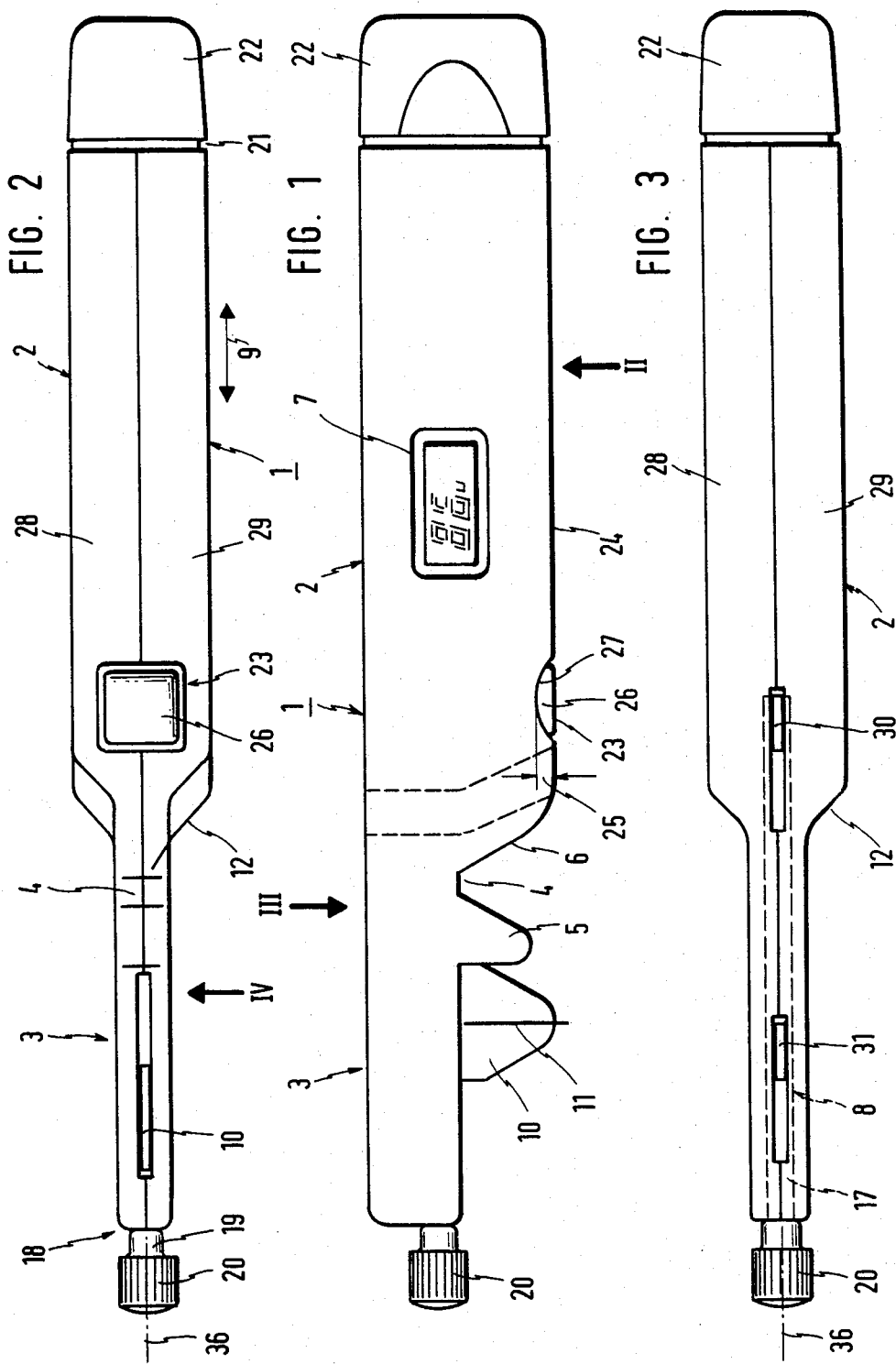

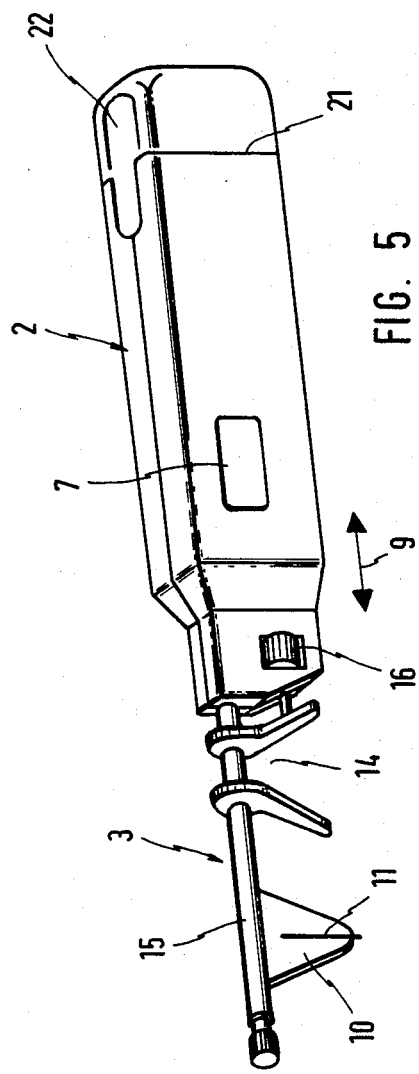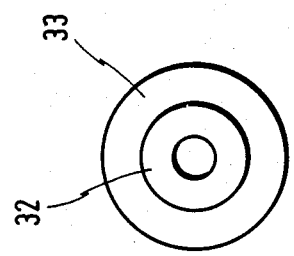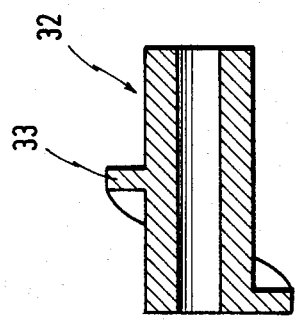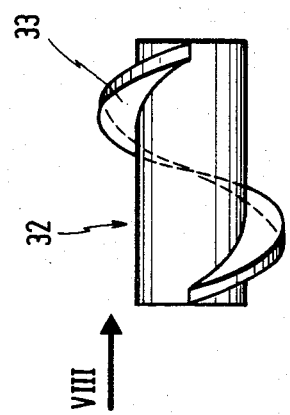

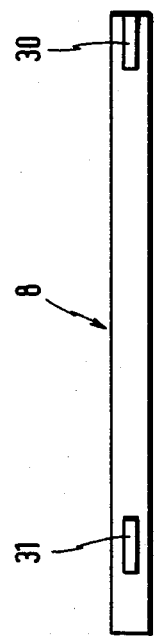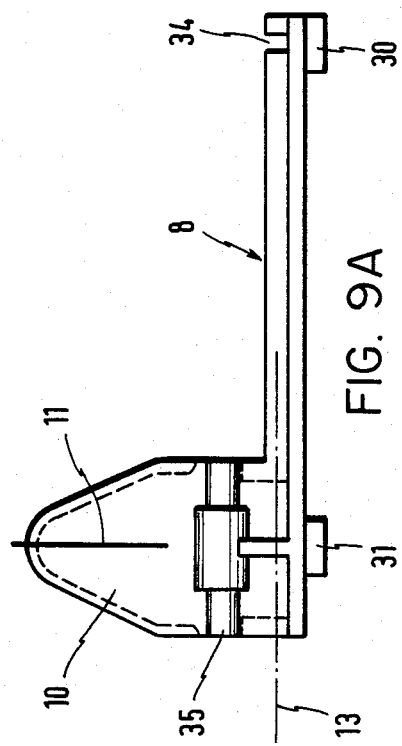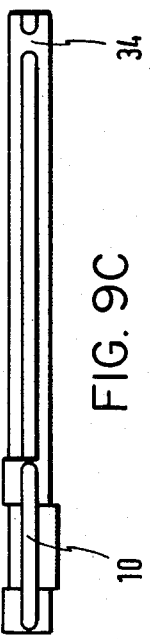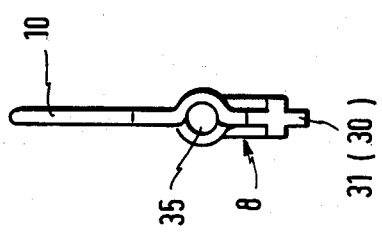

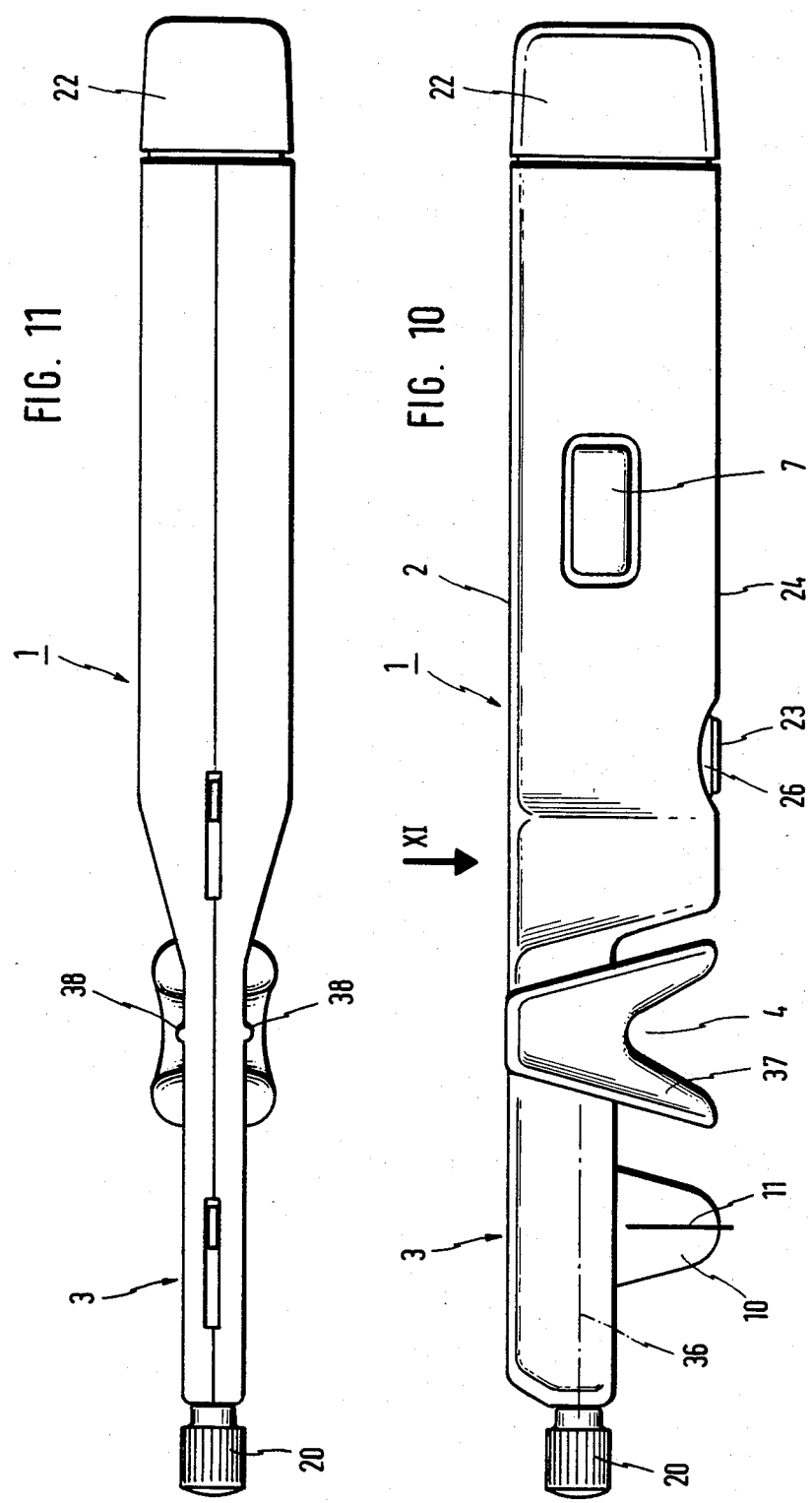

PUPILLARY DISTANCE MEASURING INSTRUMENT

This invention relates to an instrument for measuring the space between the eye and the root of the nose, comprising a sight window for reading the indication of the measured value, a part for resting on the nose and at least one slider provided with a measuring mark.

In such a known measuring instrument of this type, the part for resting on the nose is in the form of a wedge-shaped recess and is disposed approximately in the center region between the two ends of the ruler-like housing having substantially the form of a flat board. The housing is on either side of the recess provided with a through-sight opening. The distance of these through-sight openings provided on either side from the housing recess corresponds on each side approximately to the distance of the eye from the root of the nose of a human being. A slider is also arranged on either side of the housing recess so as to be movable within the housing, each slider being made of transparent material.

The shifting direction, which as a rule is horizontal, corresponds to the direction of spacing between the through-sight openings and the housing recess. In the region of the through-sight openings, the two sliders each are provided with a measuring mark or a line cross extending rectangularly to the shifting direction, i.e. vertically. Outside of the through-sight openings, each of the two sliders has an additional measuring marking which corresponds with a stationary scale division at the housing. The distance of either the left eye or the right eye from the root of the nose of a human being is measured by adjusting the line crosses of the two sliders one after the other so that each of them coincides with the center of the respective pupil and measuring the distance of the eyes via the measuring markings of the two sliders at each of the scales at the housing side. Such measuring instruments are mainly used for adapting a spectacle frame to the face of a human being.

This invention is based on the problem to construct a measuring instrument of the initially described type such that it, being of simple constructional design, is easy to handle and little space is required to accomodate it.

This problem is solved by the characterizing features of claim 1.

This solution makes it possible to measure the distance of the left eye as well as of the right eye from the root of the nose by means of one and the same slider.

An especially practical embodiment is guaranteed in those cases where a digital display is used. In contrast to the known measuring device, each indication of the measured value in case of the inventive subject matter is performed on that side of the part resting on the nose which is opposite to the measuring plate.

The actual measurement, i.e. adjustment of the relative position between slider and housing corresponding to the measuring result, is made without the use of current. It is only for reading the measuring result, in case of this digital display, that a push-button of a push-button switch is pressed into its on-position. Releasing of this pressure causes an immediate switching off of the current, i.e. extinction of the digital measuring display on either side.

The drawings show exemplifying embodiments of the inventive subject matter; said embodiments will be explained in more detail hereinafter; it is shown in FIG. 1 a side view of the measuring instrument, FIG. 2 an underside view of the measuring instrument corresponding to arrow II in FIG. 1, FIG. 3 a top view of the measuring instrument corresponding to arrow direction III in FIG. 1, FIG. 4 a top view on the front portion of an opened synthetic material semi-shell of the housing of the measuring instrument including a representation of the shifting drive corresponding to arrow IV in FIG. 2, FIG. 5 a perspective view of another embodiment of the measuring instrument, FIG. 6 a side view, FIG. 7 a vertical section, FIG. 8 a front view, corresponding to arrow VIII in FIG. 6, of the worm of the spindle drive, FIG. 9A shows an elevation view of the slider, FIG. 9B shows a top view of the slider, FIG. 9C shows a bottom view of the slider, FIG. 9D shows an end view of the slider, FIG. 9E shows a cross section view taken along line 11 of FIG. 9A, FIG. 10 a side view of a further embodiment having an exchangeable part resting on the nose, and FIG. 11 a top view on the embodiment of FIG. 10 corresponding to arrow XI.

The measuring instrument consists substantially of the housing 1 which contains the handle part 2 and the adjusting part or measuring part 3. The housing 1 is provided with a part for resting on the nose or an approximately angular recess 4 for being put on the root of the nose. The flanks 5, 6 of the recess 4 are parts of a nose crosspiece. The housing 1 on its one side is provided with a sight window 7 for a digital measuring display.

A slider 8 is mounted within the housing 1 to be movable in axial direction 9. The slider 8 is made of a transparent material, particularly synthetic material, and carries an integrally formed plate 10 having a line cross or a measuring mark 11 or has a narrow slit.

FIGS. 9A–9E show views of slider 8.

By longitudinal movement of the slider 8 in axial direction 9, the distance from the measuring mark 11 to the housing recess 4 is adjustable.

The recess 4 is arranged at the end 12, which faces toward the plate 10, of the bar-like handle part 2 forming that portion of the housing which as to volume is the substantial one. The measuring plate 10 with its measuring mark 11 is positioned on the side of the housing recess facing away from the handle part 2. The handle part 2 on either side of the longitudinal plane formed by the longitudinal slider axis 13 and the measuring plate 10 or its measuring mark 11 has a sight window 7 (FIGS. 1 and 4) so that the measured indicated value in case of the exemplifying embodiment can be read from either side of the housing; in certain cases, however, one sight window only on one side is sufficient.

In the embodiment shown in FIG. 5, the measuring plate 10 provided with the measuring mark 11 is rigidly connected to the handle part 2, whereas the nose rest 14 forming the nose crosspiece is movable in axial direction 9 by means of the slider (not shown) arranged within the handle part 2 on the cantilever 15 secured to the handle part 2. The movement is carried out via the knurled screw 16 mounted at the end of the handle part 2 facing the measuring plate 10.

In the housing 1, there is rotatably mounted, parallel to the longitudinal slider axis 13, an adjusting spindle 17 for adjusting the distance between nose rest or recess 4 or 14 and measuring plate 10. The handle end 19 of the adjusting spindle 17 in the embodiment shown in FIGS. 1 to 4 is arranged at the free end 18 of the measuring portion 3. A handle sleeve 20, which on its periphery is provided with a bordering, is put on the handle end 19 of the adjusting spindle 17.

In the two sight windows 7, there is arranged the field of vision of a digital measuring display. The handle part 2 is provided, at its rear free end 21, with an opening which can be closed by a cap 2 and is intended for receiving or inserting therein an electric battery for generating the current for the indication of the measured value. A switch serves for switching on and off the current. The switch is a push-button switch which extends rectangularly to the longitudinal slider axis, is spring-loaded in switching-off direction, and the pressure actuating end 23 of which projects from the underside 24 of the handle part 2. The projection extent 25 corresponds approximately to the extent the push-button 26 is moved from the switching-off position (FIG. 1) to the switching-on position.

The wall of the housing 2 is provided, in the region of exit of the push-button, with a depression 27 whose depth corresponds to the projection extent 25. The push-button switch is placed at the end of the handle part 2 where the housing is provided with a recess.

The housing 1 is composed of two synthetic material semi-shells one of which is partially shown in FIG. 4. The parting line plane between the two synthetic material semi-shells extends approximately in the longitudinal plane of the slider, i.e. in the direction of the central longitudinal axis 36 of the measuring instrument perpendicularly to the drawing plane in FIGS. 2 and 3. The measuring plate 10 with its measuring mark 11 projects from the housing. The slider 8 is substantially plate-shaped and is movably placed between the two synthetic material semi-shells 28,29 in the parting line plane thereof.

The slider 8 with its lateral projections 30, 31, on the one hand, and its projection forming the measuring plate 10, on the other hand, extends in housing slots which are in the form of recesses provided at the oppositely arranged side edges of the synthetic material semi-shells 28, 29.

The cross-section of the handle part 2 is approximately rectangular or elliptical, including elliptical arcs indented in the direction of the ellipse axis, the longer rectangle side or ellipse axis extending in the direction of the parting line plane or central longitudinal plane of the measuring instrument.

The worm 32 is in a torsion-proof manner put on that end of the adjusting spindle 17 which is disposed at the handle part. Its worm thread 33 meshed with a recess 34 in the slider 8. In the region of the measuring plate 10, the adjusting spindle 17 extends through the slider 8. For this purpose, the plate 10 has a through-recess 35.

In the embodiment shown in FIGS. 10 and 11, the part 4 resting on the nose is a portion of an exchange part 37 attachable to the housing 1; said part 37 can be fixedly clipped on the housing 1. To this end, the housing 1 or its measuring part 3 has on either side a form-locking elevation 38 which for example is in the form of a rail-like raised portion extending rectangularly to the central longitudinal axis 36 of the measuring instrument. The exchange part 37 can then be pre-closingly pushed on the housing 1 or its measuring part 3 from the underside 24 of the housing 1 or its measuring part 3. The recess 4 of the exchange part 37 forming the part resting on the nose is differently shaped so as to correspond to the shape of the noses. Consequently, a plurality of exchange parts corresponding to different nose shapes is delivered for one and the same measuring instrument. Prior to making the measurement, the exchange part matching with the nose of the object of measurement is selected and clipped on the housing 1 or its measuring part 3.

For measuring the distance between the one eye and the root of the nose, the housing 1 with the recess 4 is put onto the root of the nose of the face to be measured. Then the measuring mark 11 is caused to coincide the pupil of the eye by turning the adjusting spindle 17 at the handle sleeve 20 with the measuring plate 10. When the position of the pupil is exactly taken by the measuring mark 11, the measuring instrument is removed from the face. In order to make it possible to read in the sight window 7 the measuring value corresponding to the adjusted pupil distance, the push-button 26, by which the current supply of the digital measuring display is switched on, is depressed. When the measurement value of the one eye has been determined, the instrument in its horizontal position is turned about a vertical axis by about 180° and taken in the other hand of the operator. Now the housing recess 4 is again put onto the root of the nose—now from the other side—and the second measurement is made for the other eye, as described in the foregoing. The indication of the measured value corresponding to the measurement result can again be read only after the push-button has been actuated in the sight window 7 provided at the side of the handle part 2 facing toward the operator.

I claim:

1. An instrument for measuring the distance of the eye from the root of the nose comprising a housing having a handle portion adapted for gripping by the hand of a user, said handle portion further having recesses therein for receiving a battery and a battery-operated display device, said housing further having a nose piece portion for resting on the root of the nose, said housing further having a measurement portion with interior recesses and at least one slot through said housing in said measurement portion; a slider in said housing measurement portion, said slider having a transparent plate projecting therefrom and through said slot, said plate having an eye index mark thereon; a rotatable shaft projecting from the measurement portion of the housing at one of its ends, and into the interior recesses of said measurement portion at its other end; means for drivingly coupling said shaft interior end to said slider, whereby rotation of said shaft causes said slider plate to linearly move relative to said nose piece.

2. The apparatus of claim 1 wherein said nose piece portion is removably attached to said housing.

3. An instrument for measuring the distance of an eye from the root of the nose, comprising
    a housing having a plurality of recesses therein and having a nose piece affixed thereto for resting on the root of the nose, said housing having a handle portion extending in a first direction from said nose piece and having a slotted measurement portion extending in a second opposite direction from said nose piece;
    a slider in said housing measurement portion, said slider having a measurement plate projecting through said slotted measurement portion, said measurement plate having an index line thereon;

a rotatable shaft having a screw on a first end in said housing and having a second end projecting outside said housing;

means for engaging said screw against said slider whereby rotatable motion of said shaft causes linear motion of said slider and said measurement plate relative to said nose piece; and means for containing a battery and battery-operated visual display in the handle portion of said housing, including means for actuating said visual display to provide a representation of the relative position of said index line and said nose piece.

4. The apparatus of claim 3 further comprising an electrical switch in said handle portion, said switch connected between said battery and said visual display to control the electrical power to actuate said visual display.

5. The apparatus of claim 3, wherein said housing further comprises two sections which are attachable together.

6. The apparatus of claim 5, wherein said measurement plate is constructed of transparent material.

* * * * *